US009789269B2

(12) United States Patent
Colomb et al.

(10) Patent No.: US 9,789,269 B2
(45) Date of Patent: Oct. 17, 2017

(54) DEVICE FOR DISPENSING A FLUID PRODUCT

(75) Inventors: Arnaud Colomb, Verneuil sur Seine (FR); Zakaria Sallak, Rouen (FR)

(73) Assignee: APTAR FRANCE SAS, Le Neubourg (FR)

( * ) Notice: Subject to any disclaimer, the term of this patent is extended or adjusted under 35 U.S.C. 154(b) by 834 days.

(21) Appl. No.: 13/703,197

(22) PCT Filed: Jun. 9, 2011

(86) PCT No.: PCT/FR2011/051311
§ 371 (c)(1),
(2), (4) Date: Dec. 10, 2012

(87) PCT Pub. No.: WO2011/154659
PCT Pub. Date: Dec. 15, 2011

(65) Prior Publication Data
US 2013/0139815 A1 Jun. 6, 2013

(30) Foreign Application Priority Data
Jun. 11, 2010 (FR) ...................................... 10 54626

(51) Int. Cl.
*A61M 15/00* (2006.01)
(52) U.S. Cl.
CPC ...... *A61M 15/0045* (2013.01); *A61M 15/004* (2014.02); *A61M 15/0008* (2014.02);
(Continued)
(58) Field of Classification Search
USPC .......... 604/58; 206/528, 530, 533, 535, 538, 206/539; 128/203.15, 203.19, 203.21
See application file for complete search history.

(56) References Cited

U.S. PATENT DOCUMENTS 5,261,548 A * 11/1993 Barker ...................... A61J 7/02
206/534
5,349,945 A * 9/1994 Wass ................... A61M 15/009
128/200.14
(Continued)

FOREIGN PATENT DOCUMENTS

WO 2008/012456 A2 1/2008
WO 2009/077697 A1 6/2009

*Primary Examiner* — Tan-Uyen (Jackie) T Ho
*Assistant Examiner* — Joseph D Boecker
(74) *Attorney, Agent, or Firm* — Sughrue Mion, PLLC

(57) ABSTRACT

A fluid dispenser device comprising: a dose counter for indicating the number of doses that have been dispensed or that remain to be dispensed, said counter comprising: at least one rotary counter element provided with indicator means, such as digits or numbers, and provided with a first set of teeth and with a second set of teeth; a movable actuator element adapted to co-operate with said first set of teeth of said counter element so as to turn it; and anti-return means adapted to co-operate with said second set of teeth so as to prevent said counter element from turning in the direction opposite to the direction that is imposed by said actuator element; said anti-return means comprising a tip that is substantially V-shaped, and that, after each actuation of the counter, co-operates with a respective tooth of said second set of teeth in a blocking position, said tip comprising a first branch that is adapted to co-operate in the blocking position with a blocking shoulder of said tooth, and a second branch that is plane and adapted to co-operate with a plane surface of said teeth, said plane second branch and said plane surface being coplanar when said tip is in the blocking position, said tip being urged resiliently towards said blocking position so as to ensure accurate positioning of said counter element after each actuation of the counter.

7 Claims, 1 Drawing Sheet

(52) U.S. Cl.
CPC .... *A61M 15/0026* (2014.02); *A61M 15/0033* (2014.02); *A61M 15/0051* (2014.02); *A61M 15/0055* (2014.02); *A61M 15/0065* (2013.01); *A61M 15/0075* (2014.02); *A61M 15/0091* (2013.01); *A61M 15/0096* (2014.02); *A61M 2202/064* (2013.01)

(56) References Cited

U.S. PATENT DOCUMENTS

| | | | | |
|---|---|---|---|---|
| 5,590,645 | A * | 1/1997 | Davies | A61M 15/0045 128/203.15 |
| 5,871,007 | A * | 2/1999 | Clark, Jr. | A61M 15/009 128/200.14 |
| 5,988,496 | A * | 11/1999 | Bruna | G06M 1/041 222/18 |
| 6,056,169 | A * | 5/2000 | Bruna | A61M 15/0065 222/636 |
| 2005/0209558 | A1 * | 9/2005 | Marx | A61M 15/009 604/97.03 |
| 2006/0096594 | A1 * | 5/2006 | Bonney | A61M 15/0065 128/202.17 |
| 2007/0246042 | A1 * | 10/2007 | Purkins | A61M 15/0065 128/200.14 |
| 2008/0035144 | A1 * | 2/2008 | Bowman | A61M 15/009 128/203.15 |
| 2009/0178677 | A1 * | 7/2009 | Pocock | A61M 15/0045 128/203.15 |
| 2009/0283095 | A1 * | 11/2009 | Pocock | A61M 15/0045 128/203.15 |
| 2009/0308389 | A1 | 12/2009 | Pocock et al. | |
| 2010/0012119 | A1 * | 1/2010 | Sallak | A61M 15/0045 128/203.15 |
| 2010/0175697 | A1 * | 7/2010 | Massot | A61M 15/0045 128/203.15 |
| 2010/0229855 | A1 * | 9/2010 | Howgill | A61M 15/009 128/200.23 |
| 2010/0258120 | A1 * | 10/2010 | Colomb | A61M 15/0045 128/203.21 |
| 2010/0258121 | A1 * | 10/2010 | Kirniak | A61M 15/0096 128/203.21 |
| 2010/0263668 | A1 * | 10/2010 | Sallak | A61M 15/0045 128/203.15 |
| 2011/0036349 | A1 * | 2/2011 | Colomb | A61M 15/0045 128/203.15 |
| 2012/0152245 | A1 * | 6/2012 | Rolfs | A61M 15/0045 128/203.15 |

\* cited by examiner

DEVICE FOR DISPENSING A FLUID PRODUCT

CROSS REFERENCE TO RELATED APPLICATIONS

This application is a National Stage of International Application No. PCT/JP2011/051311, filed on Jun. 9, 2011, which claims priority from French Patent Application No. 1054626, filed on Jun. 11, 2010, the contents of all of which are incorporated herein by reference in their entirety.

The present invention relates to a fluid dispenser device, and more particularly to a dry-powder inhaler.

Dry-powder inhalers are well known in the prior art. Various types exist. A first type of inhaler contains a reservoir receiving many doses of powder, the inhaler being provided with metering means making it possible, on each actuation, to remove one dose of said powder from the reservoir, so as to bring said dose into an expulsion duct in order to be dispensed to the user. Another type of inhaler consists in packaging the doses of powder in individual predosed reservoirs, then in opening one of the reservoirs each time the inhaler is actuated. That implementation seals the powder more effectively since each dose is opened only when it is about to be expelled. In order to make such individual reservoirs, various techniques have already been proposed, such as an elongate blister strip or blisters disposed on a rotary circular disk. Inhalers including individual reservoirs, such as capsules, that are loaded into the inhaler just before said reservoir is used are also described in the prior art. The advantage of such devices is that it is not necessary to store all of the doses inside the appliance, such that said appliance can be compact. Obviously however, the inhaler is more difficult to use, since the user is obliged to load a capsule into the inhaler before each use. All existing types of inhalers, including those described above, present both advantages and drawbacks associated with their structures and with their types of operation. Thus, with certain inhalers, there is the problem of metering accuracy and reproducibility on each actuation. In addition, the effectiveness of the dispensing, i.e. the fraction of the dose that effectively penetrates into the user's lungs in order to have a beneficial therapeutic effect, is also a problem that exists with a certain number of inhalers. A solution for solving that specific problem has been to synchronize the expulsion of the dose with the inhalation of the patient. Once again, that can create drawbacks, in particular in that type of device, the dose is generally loaded into an expulsion duct before inhalation, then expulsion is synchronized with inhalation. That means that if the user drops, shakes, or manipulates the inhaler in an undesirable or inappropriate manner between the moment when the user loads the dose (either from a multidose reservoir or from an individual reservoir) and the moment when the user inhales, then the user risks losing all or part of the dose, with said dose possibly being spread about inside the appliance. In that event, there can exist a high risk of overdosing the next time the device is used. The user who realizes that the dose is not complete will load a new dose into the appliance, and while the new dose is being inhaled, a fraction of the previous dose that was lost in the appliance could thus be expelled at the same time as the new dose, thereby causing an overdose. In the treatments envisaged, such overdosing can be very harmful, and the authorities in all countries are issuing ever-stricter requirements to limit the risk of overdosing as much as possible. With regard to opening the individual reservoirs, it has been proposed to peel off or to unstick the closure layer. That presents the drawback of difficulty in controlling the forces to be applied in order to guarantee complete opening, without running the risk of opening the next reservoir, particularly if the opening means need to be actuated by inhalation. In a variant, it has been proposed to perforate the closure layer or wall. That can present the drawback that the cut wall-portions risk retaining a fraction of the dose inside the reservoir, so that metering accuracy and reproducibility are therefore not guaranteed. In addition, it is known to use a dose counter or indicator for informing the user about the number of doses that have been dispensed or that remain to be dispensed. A conventional drawback with such counters is that either they are very bulky, correspondingly increasing the size of the inhaler itself, or the display is very small and often difficult to read, in particular for the elderly. In particular, this is true for counters for counting any number of doses, e.g. 30 or 60 doses. In addition, in order to optimize the display, the dimensions of the viewing window of the counters are generally close to the dimensions of the numbers to be displayed. It follows that if the number to be displayed is not well centered relative to said window, the display is not satisfactory. Document WO 2009/077697 describes a counter for an inhaler to which the present invention can be applied.

An object of the present invention is to provide a fluid dispenser device, in particular a dry-powder inhaler, that does not have the above-mentioned drawbacks.

In particular, an object of the present invention is to provide a device that is simple and inexpensive to manufacture and to assemble, that is reliable in use, guaranteeing metering accuracy and metering reproducibility on each actuation, providing an optimum yield with regard to the effectiveness of the treatment, by making it possible to dispense a substantial fraction of the dose to the zones to be treated, in particular the lungs, avoiding, in safe and effective manner, any risk of overdosing, and that is as compact as possible, while guaranteeing sealing and absolute integrity of all of the doses up to their expulsion.

Another object of the present invention is to provide a device that makes it possible to count the number of doses that have been emitted or that remain to be emitted and that is of reasonable size, while proposing a display that is reliable and clearly readable by the users after each actuation.

The present invention thus provides a fluid dispenser device comprising: a body provided with a dispenser orifice; a plurality of individual reservoirs each containing one dose of powder; dispenser means for dispensing one dose of powder on each actuation, said dispenser means including reservoir opening means for opening a respective reservoir on each actuation and for releasing the dose of powder; and a dose counter for indicating the number of doses that have been dispensed or that remain to be dispensed, said counter comprising: at least one rotary counter element provided with indicator means, such as digits or numbers, and provided with a first set of teeth and with a second set of teeth; a movable actuator element adapted to co-operate with said first set of teeth of said counter element so as to turn it; and anti-return means adapted to co-operate with said second set of teeth so as to prevent said counter element from turning in the direction opposite to the direction that is imposed by said actuator element; the device being characterized in that said anti-return means comprise a tip that is substantially V-shaped, and that, after each actuation of the counter, co-operates with a respective tooth of said second set of teeth in a blocking position, said tip comprising a first branch that is adapted to co-operate in the blocking position with a blocking shoulder of said tooth, and a second branch that is plane and adapted to co-operate with a plane surface of said teeth, said plane second branch and said plane surface being coplanar when said tip is in the blocking position, said tip being urged resiliently towards said blocking position so as to ensure accurate positioning of said counter element after each actuation of the counter.

Advantageously, said anti-return means are substantially S-shaped, with a first loop providing springiness, and a second loop forming the tip.

Advantageously, the two ends of the S are connected to a stationary portion of said body.

Advantageously, on each actuation of the counter, said actuator element provides a major portion of the turning of the counter element, said tip providing the final portion of said turning.

These characteristics and advantages and others of the present invention appear more clearly from the following detailed description of several embodiments and variants thereof, given by way of non-limiting example, and with reference to the accompanying drawings, and in which.

Figure 1:
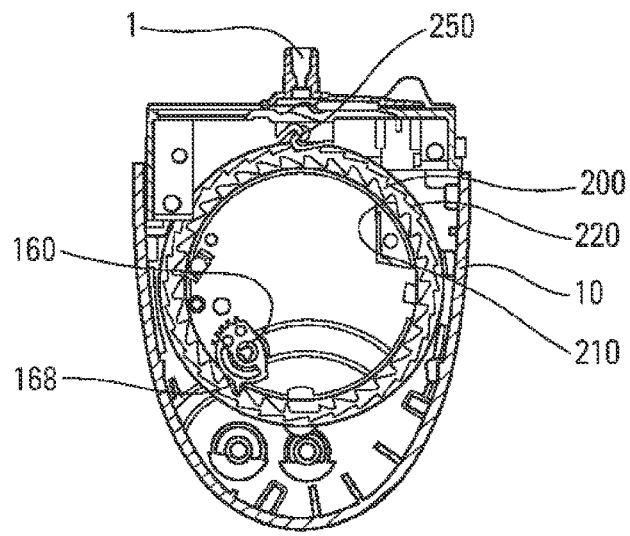
FIG. 1 is a fragmentary and diagrammatic section view of a fluid dispenser device in an advantageous embodiment of the present invention.

FIG. 1 shows an advantageous embodiment of a dry-powder inhaler. The inhaler includes a body 10 on which there can be slidably mounted two cap-forming portions (not shown) that are adapted to be opened so as to open and load the device. The body 10 can be approximately rounded in shape, as shown in the figures, but it could be of any other appropriate shape. The body 10 includes a mouthpiece or inhaler endpiece 1 that defines a dispenser orifice through which the user inhales while the device is being actuated. The caps can be opened by pivoting about a common pivot axis, but any other opening means can be envisaged for opening the device. In a variant, the device could include a single cover instead of two.

Inside the body 10 there is preferably provided a strip (not shown) of individual reservoirs, also known as blisters, said strip being made in the form of an elongate strip on which the blisters are disposed one behind another, in manner known per se. The blisters, preferably containing powder, are not shown in FIG. 1, so as to avoid cluttering the drawings for the purpose of clarity. The blister strip is advantageously constituted by a base layer or wall that forms the cavities receiving the doses of powder, and by a closure layer or wall that covers each of said blisters in sealed manner. Before first use, the blister strip can be rolled-up inside the body 10, preferably in a storage portion, and first strip displacement means (not shown), in particular rotary means, are provided for progressively unrolling the blister strip and for causing it to advance. Second displacement means, in particular means mounted to pivot on the body 10, are provided for bringing a respective blister or individual reservoir into a dispensing position each time the device is actuated. The strip portion including the empty reservoirs is advantageously adapted to be rolled-up at another location of said body 10, preferably a reception portion.

The inhaler includes reservoir opening means (not shown) preferably comprising perforator and/or cutter means for perforating and/or cutting the closure layer of the blisters. For example, the reservoir opening means advantageously comprise a needle that is preferably stationary relative to the body 10, and against which a respective blister is displaced on each actuation by the second displacement means. The blister is thus perforated by said needle, which penetrates into said blister so as to expel the powder by means of the suction of the user inhaling.

The first displacement means are adapted to cause the blister strip to advance before and/or during and/or after each actuation of the device. The second displacement means are adapted to displace the reservoir to be emptied against said perforator and/or cutter means during actuation. The second displacement means can be urged by a resilient element, such as a spring or any other equivalent resilient element, said resilient element being suitable for being prestressed while the device is being opened. Preferably, the first displacement means comprise an indexer wheel that receives and guides the blisters. Turning the wheel causes the blister strip to advance. In a particular angular position, a given reservoir is always in a position facing the opening means. The second displacement means can include a support element that is mounted to pivot about a pivot axis, said indexer wheel being rotatably mounted on said support element.

An actuation cycle of the device can be as follows. While the device is being opened, the two cap-forming lateral portions are moved apart by pivoting on the body in order to open the device and thus pre-stress the device. In this position, the indexer wheel cannot be displaced towards the needle, since the second displacement means are held by appropriate blocking means. Preferably, it is while the user is inhaling through the mouthpiece 1 that the blocking means are unblocked, thereby causing said indexer wheel to be displaced towards the needle, and thus causing a reservoir to be opened.

As explained above, it is desirable for the opening means to be actuated by the user inhaling. In order to trigger the reservoir opening means by inhalation, an inhalation trigger system is provided that advantageously comprises a unit (not shown) that is displaceable and/or deformable under the effect of inhalation, the unit being adapted to release the blocking means. The unit advantageously comprises a deformable air-chamber. Inhalation by the user causes said deformable air-chamber to deform, thereby making it possible to release said blocking means and to enable the second displacement means to be displaced, and therefore to enable a respective reservoir to be displaced towards its opening position. The reservoir is therefore opened only on inhalation, such that it is emptied simultaneously. Thus, there is no risk of any of the dose being lost between opening the reservoir and emptying it.

In a variant, other inhalation trigger means could also be used, e.g. using a pivotable valve flap that, while the user is inhaling, pivots under the effect of the suction created by the inhalation, with pivoting of the valve flap causing the blocking means blocking the movable support means to be released, thereby causing the reservoir to be displaced towards the opening means.

The inhaler further includes a dispenser or dispersion chamber (not shown) for receiving the dose of powder after a respective reservoir has been opened. Advantageously, the dispenser chamber is provided with at least one bead (not shown) that is displaced inside said chamber during inhalation so as to improve the dispensing of the air and powder mixture after a reservoir has been opened, in order to increase the effectiveness of the device.

After inhalation, when the user closes the device, all of the components return to their initial, rest positions. The device is thus ready for a new utilization cycle.

The body advantageously includes a window 19 through which the number of doses that have been dispensed or that remain to be dispensed can be displayed in visible manner for the user. By way of example, the window can be provided on or close to the pivot axis of the cover-forming cover elements, but it could be in another location.

The device of the invention includes a dose indicator or counter that is adapted to count or indicate to the user the number of doses that have been dispensed or that remain to be dispensed. Document WO 2009/077697 describes a counter to which the present invention applies. The indicator includes at least one rotary counter element 200, advantageously made in the form of a ring, provided with a first set of teeth 210 and with a second set of teeth 220 and including indicator means 125, e.g. digits or numbers, provided on one of its surfaces. Preferably, the indicator means 125 are disposed on a top surface, whereas the sets of teeth 210, 220 are disposed on a bottom surface. The first set of teeth 210 is advantageously adapted to co-operate with an actuator element or an actuator 160, whereas the second set of teeth 220 is advantageously adapted to co-operate with anti-return means 250 that are adapted to prevent the counter element 200 from turning in the direction opposite to the direction that is imposed thereto by the actuator 160.

Figure 2:
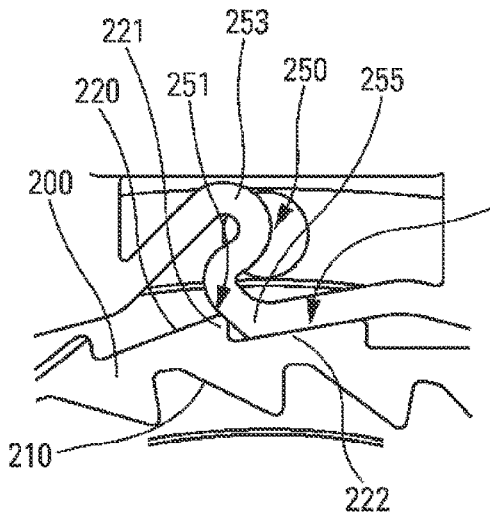
FIG. 2 is view of a detail of the FIG. 1 anti-return means, before and after actuation of the counter.
Figure 3:
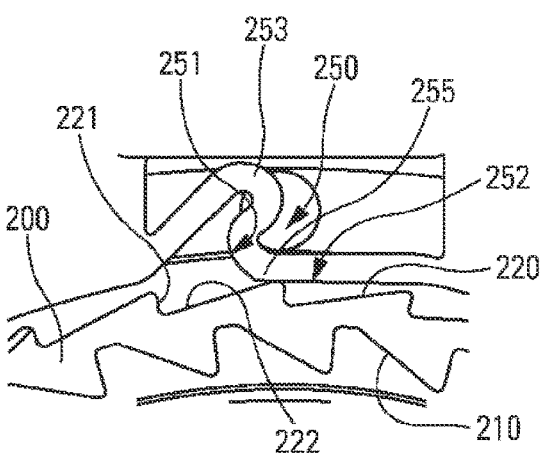
FIG. 3 is view similar to the view in FIG. 2, during actuation of the counter.

In the invention, the anti-return means also act as centering means so as to ensure accurate positioning of the counter element 200, and thus good centering of the indicator means 125 in the window 19, after each actuation. The anti-return means comprise a tip 255 that is substantially V-shaped, and that, after each actuation of the counter, co-operates with a respective tooth of said second set of teeth 220 in a blocking position. As can be seen in FIGS. 2 and 3, said tip 255 comprises a first branch 251 that is adapted to co-operate in the blocking position with a blocking shoulder 221 of said tooth, and a plane second branch 252 that is adapted to co-operate with a plane surface 222 of said teeth. Said plane second branch 252 and said plane surface 222 are coplanar when said tip 255 is in the blocking position, and said tip 255 is urged resiliently towards said blocking position so as to ensure accurate positioning of said counter element 200 after each actuation of the counter.

Preferably, said anti-return means are substantially S-shaped. In FIGS. 2 and 3, the S is back to front, but obviously it could also be formed the other way round. The S-shape comprises two loops, a first loop 253 to provide springiness, and a second loop forming said tip 255. Advantageously, the two ends of the S are connected to a stationary portion of the body 10. This improves the reliability and the lifetime of said anti-return means. The S-shape is intrinsically robust, and the fact that the two ends of the S are fastened to the body eliminates any risk of malfunctioning even after several actuations.

Figure 4:
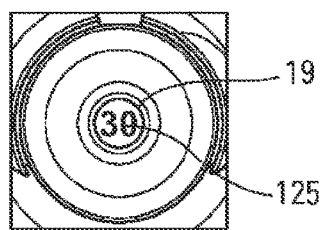
FIGS. 4 to 6 are diagrammatic views of the display of the counter, respectively before, during, and after an actuation of the counter.

As can be seen in FIGS. 2 and 3, the first branch 251 that co-operates with the blocking shoulder 221 of the tooth may be curved, a single contact point sufficing to ensure blocking. In contrast, the second branch 252 matches the plane portion 222 of the tooth, so as to ensure the accurate angular positioning of the counter element 200. Naturally, if the portion 222 of the tooth was not exactly plane, the second branch 252 would not be exactly plane either. It is these two surfaces in coplaner contact in the blocking position that ensure accurate positioning, unlike the anti-return means described in document WO 2009/077697, in which the tip of the anti-return tab does not makes it possible to guarantee accurate angular positioning after each actuation. As can be seen in particular in FIGS. 4 to 6, the display of the indicator means 125, specifically the numbers 30 and 29, take up all of the surface area of the window 19. Thus, even a small angular offset would risk truncating the displayed number. In contrast, because of the V-shape of the tip 255, with a branch of the V in coplanar contact with the tooth, the display is always accurate and centered, as can be seen in FIGS. 4 and 6.

During actuation of the counter, when the counter element 200 turns, the tip 255 slides over the plane surface 222 of the tooth, as can be seen in FIG. 3, elastically deforming the S like a spring. When the S passes over the shoulder 221 of the next tooth, the tip 255 snaps into the next tooth under the effect of the springiness of the S. The same springiness urges said tip 255 until the plane second branch 252 is flush with the plane surface 222 of the tooth. In this position, in particular because of the slope of said plane surface 222, the tip is also pushed into contact with the shoulder 221. Thus, after each actuation, the tip 255 is situated accurately in the same position relative to the tooth with which it co-operates. Since the S is deformable radially but not angularly, the angular position of the counter element is thus accurately defined.

Advantageously, the major portion of the turning of the counter element 200, e.g. up to at least 75%, preferably up to about 90%, is provided by said actuator element 160, the remainder being provided at the end of turning by said anti-return means, and in particular said tip 255, under the effect of restoring energy that was accumulated during the elastic deformation of said S at the start of turning. This avoids any risk of incomplete counting of a dose, the complete angular turning of the counter element being guaranteed on each dose, firstly by the actuator element and then by the anti-return means.

Advantageously, the counter avoids counting doses that have not been dispensed, e.g. in the event of a manipulation error, or of an incomplete manipulation of the device. Provision is thus made for the counter to be actuated only once the user has inhaled, since it is this inhalation that makes it possible for the blister to open and the dose contained therein to be dispensed. To do this, the device may include an actuator or actuator element 160 that is pivotally mounted on the body 10 and meshed with the second displacement means. Thus, when the user opens the device and stresses the stressing means of the device, the second displacement means do not move since they are held in the non-dispensing position by the blocking means. Thus, nothing happens to the counter since the actuator 160 that is pivotally mounted on the body 10 and meshed with the second displacement means, also remains stationary. If the user closes the device without inhaling, obviously still nothing happens since the second displacement means still remain stationary. In this way, it is guaranteed that the counter does not count doses if there is no inhalation. From the stressed position, if the user inhales, the second displacement means are displaced into their dispensing position towards the opening means. This displacement thus causes the actuator 160 to pivot. The actuator 160 may include a finger 168 that meshes in the first set of teeth 210 of the counter element 200, as can be seen in FIG. 1. In the first displacement direction, the finger 168 of the actuator can slide over the slope of the corresponding tooth so as to become positioned facing the next tooth. In parallel, the anti-return means 250 co-operate with the second set of teeth 220 of the counter element 200 so as to prevent said counter element from turning under the effect of friction, e.g. exerted by the finger 168 of the actuator on the first set of teeth 210. After inhalation, when the user closes the device, the second displacement means are returned to their rest position, i.e. the non-dispensing position. This movement thus causes the actuator 160 to pivot in the opposite direction. In this displacement in the opposite direction, the finger 168 of the actuator 160 presses into the tooth in which it is positioned so as to cause the counter element 200 to turn. In parallel, the anti-return means 250 slide over the slope 222 of the tooth so as to become positioned in the following tooth of the second set of teeth 220, once again ensuring that it is centered, as described above. In a variant, the counter element 200 could be turned while the second displacement means are being displaced towards their dispensing position, e.g. reversing the direction of the teeth of the first set of teeth 210. Still in a variant, the first and second sets of teeth could be formed by a single peripheral set of teeth in place of two separate sets of teeth as shown in FIG. 1.

Figure 5:
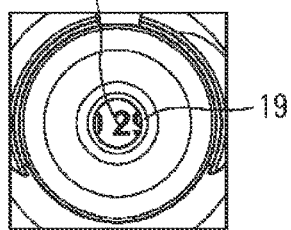
Figure 6:
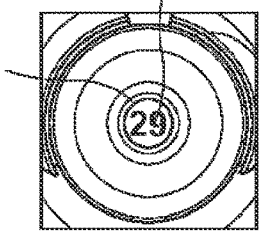

The counter may be adapted to indicate the number of doses that remain to be dispensed, so that the number displayed decreases on each actuation, as shown in FIGS. 4 to 6. Naturally, the inverse is also possible, namely a counter that counts the number of doses that have been dispensed. Advantageously, it is possible to provide blocking means for blocking the indicator after the last dose has been dispensed. The blocking means can take different forms, an advantageous form being to provide a tooth of different shape on the first set of teeth 210 so that the actuator can no longer become meshed in the next tooth in order to continue causing said indicator ring to turn. Other means for preventing the first ring from turning after the last dose has been dispensed can also be envisaged.

The counter is described above with one counter element, but naturally it may include at least a second counter element, as described in document WO 2009/077697, so as to make it possible to count a greater number of doses.

The present invention therefore makes it possible to provide a dry-powder inhaler that provides the following features:
- a plurality of individual doses of powder stored in individual sealed reservoirs, e.g. 30 or 60 doses stored on a rolled-up strip;
- the powder is released by perforation that is achieved by the user inhaling, the blister being perforated by means of an inhalation detector system that is coupled to a pre-stressed release system;
- appropriately-shaped drive means that are engaged with blisters so as to displace the blister strip on each actuation, and bring a new reservoir into a position in which it is to be opened by appropriate opening means;
- means for avoiding doses being lost in the event of the inhaler being opened, but in the absence of any inhalation. In this event, when the inhaler closes, the device returns exactly to its start position; and
- a dose indicator adapted to count the doses only in the event of inhalation, and guaranteeing a readable display on each actuation.

Other features are also provided by the device of the invention as described above. It should be observed that the various features, even if they are shown as being provided simultaneously on the various embodiments of the inhaler, could be implemented separately. In particular, the inhalation trigger mechanism could be used regardless of the type of reservoir opening means, regardless of the use of a dose indicator, regardless of the way in which the individual reservoirs are arranged relative to one another, etc. The cocking means and the inhalation trigger system could be made in some other way. The same applies for other component parts of the device.

Various modifications may also be envisaged by a person skilled in the art, without going beyond the ambit of the present invention, as defined by the accompanying claims. In particular, the various characteristics and functions of the device described with reference to the various embodiments and variants can be adapted to all of the embodiments and variants, and can be combined together in any appropriate manner.

The invention claimed is:

1. A fluid dispenser device comprising: a body provided with a dispenser orifice; a plurality of individual reservoirs each containing one dose of powder; dispenser means for dispensing one dose of powder on each actuation, said dispenser means including reservoir opening means for opening a respective reservoir on each actuation and for releasing the dose of powder; and a dose counter for indicating the number of doses that have been dispensed or that remain to be dispensed, said counter comprising: at least one rotary counter element provided with indicator means, and provided with a first set of teeth and with a second set of teeth; a movable actuator element adapted to co-operate with said first set of teeth of said counter element so as to turn said counter element; and anti-return means adapted to co-operate with said second set of teeth so as to prevent said counter element from turning in the direction opposite to the direction that is imposed by said actuator element; wherein said anti-return means comprise a tip that is substantially V-shaped, and that, after each actuation of the counter, co-operates with a respective tooth of said second set of teeth in a blocking position, said tip comprising a first branch that is adapted to cooperate in the blocking position with a blocking shoulder of said tooth, and a second branch that is plane and adapted to co-operate with a plane surface of said teeth, said plane second branch and said plane surface being coplanar when said tip is in the blocking position, said tip being urged resiliently towards said blocking position so as to ensure accurate positioning of said counter element after each actuation of the counter;
   wherein said anti-return means are substantially S-shaped, with a first loop providing springiness, and a second loop forming the tip; and
   wherein ends of the S-shape are connected to a stationary portion of said body; and
   wherein the first loop of the S-shape elastically deforms upon actuation of the dispenser during which opposing segments of the first loop are squeezed bringing the opposing segments into closer proximity to each other.

2. The device according to claim 1, wherein, on each actuation of the counter, turning of the counter element is primarily due to the actuator element, said tip contributing to a final portion of said turning.

3. The device according to claim 1, wherein the indicator means are digits or numbers.

4. A fluid dispenser device comprising:
   a body provided with a dispenser orifice;
   a plurality of individual reservoirs each containing one dose of powder that is released on each actuation of the dispenser and dispensed through the dispenser orifice; and
   a dose counter for indicating the number of doses that have been dispensed or that remain to be dispensed, the dose counter comprises:

at least one rotary counter element provided with indications and with a first set of teeth and a second set of teeth;

a movable actuator adapted to co-operate with the first set of teeth so as to turn the counter element; and an anti-return mechanism adapted to co-operate with the second set of teeth so as to prevent the counter element from turning in a direction opposite to a direction that is imposed by the actuator element;

wherein the anti-return mechanism comprises a tip that is substantially V-shaped, and that, after each actuation of the rotary counter, co-operates with a respective tooth of the second set of teeth in a blocking position, the tip comprising a first branch that is adapted to cooperate in the blocking position with a corresponding blocking shoulder of the tooth, and a second branch that is adapted to be flush with a surface of the teeth when the tip is in the blocking position, the tip being urged resiliently towards the blocking position so as to ensure accurate positioning of the counter element after each actuation of the counter element; and wherein the anti-return mechanism is substantially S-shaped, with a first loop providing springiness, and a second loop forming the tip;

wherein ends of the S-shape are connected to a stationary portion of the body; and wherein the first loop of the S-shape elastically deforms upon actuation of the rotary counter during which opposing segments of the first loop that form half of the S-shape elastically compress bringing the opposing segments closer together.

5. The device according to claim 4, wherein the second branch is planar and the surface of the teeth is coplanar when the second branch is flush with the surface.

6. The device according to claim 5, wherein the first branch is curved.

7. The device according to claim 4, wherein the S-shape is deformable radially with respect to the rotary counter element.

* * * * *